United States Patent [19]

Nedelec et al.

[11] 4,117,164
[45] Sep. 26, 1978

[54] AMINOMETHYL-BENZOCYCLOHEPTENES AND METHOD OF USE

[75] Inventors: Lucien Nedelec, Le Raincy; Daniel Frechet, Paris; Claude Dumont, Nogent-sur-Marne, all of France

[73] Assignee: Roussel Uclaf, Paris, France

[21] Appl. No.: 850,273

[22] Filed: Nov. 10, 1977

[30] Foreign Application Priority Data

Nov. 17, 1976 [FR] France .................. 76 34597

[51] Int. Cl.$^2$ .................. A01N 9/20; C07C 87/28
[52] U.S. Cl. .................. 424/330; 260/465 E; 260/465 F; 260/465 K; 260/501.1; 260/501.18; 260/501.19; 260/570.9; 260/590 FA; 424/316; 560/19
[58] Field of Search .......... 260/570.9, 581.1, 501.18, 260/501.19; 424/316, 330

[56] References Cited

U.S. PATENT DOCUMENTS

| 2,441,069 | 5/1948 | Hoffmann et al. ............ 260/570.9 X |
| 2,794,048 | 5/1957 | Richter et al. ............... 260/570.9 |
| 3,706,765 | 12/1972 | Wilhelm ..................... 260/570.9 X |
| 3,981,917 | 9/1976 | Engelhardt .................. 260/570.9 X |

Primary Examiner—Robert V. Hines
Attorney, Agent, or Firm—Hammond & Littell

[57] ABSTRACT

Novel 7-aminomethyl-benzocycloheptenes of the formula

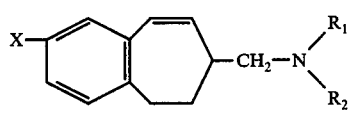

wherein X is selected from the group consisting of nitro, amino, methoxy and hydroxy, $R_1$ is selected from the group consisting of hydrogen and alkyl of 1 to 5 carbon atoms and $R_2$ is alkyl of 1 to 5 carbon atoms and their non-toxic, pharmaceutically acceptable acid addition salts having antidepressant activity and their preparation.

14 Claims, No Drawings

AMINOMETHYL-BENZOCYCLOHEPTENES AND METHOD OF USE

STATE OF THE ART

Copending, commonly assigned U.S. Pat. applications Ser. No. 713,817 and Ser. No. 713,818, both filed on Aug. 12, 1976 describe aminomethyl-benzocycloheptenes.

OBJECTS OF THE INVENTION

It is an object of the invention to provide the novel 7-aminomethyl-benzocycloheptenes of formula I and their non-toxic, pharmaceutically acceptable acid addition salts and to a novel process for their preparation and novel intermediates.

It is another object of the invention to provide novel antidepressant compositions and to provide a novel method of relieving depression in warm-blooded animals.

These and other objects and advantages of the invention will become obvious from the following detailed description.

THE INVENTION

The novel compounds of the invention are selected from the group consisting of 7-aminomethyl-benzocycloheptenes of the formula

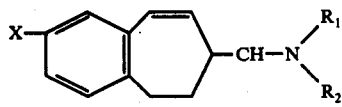

wherein X is selected from the group consisting of nitro, amino, methoxy and hydroxy, $R_1$ is selected from the group consisting of hydrogen and alkyl of 1 to 5 carbon atoms and $R_2$ is alkyl of 1 to 5 carbon atoms and their non-toxic, pharmaceutically acceptable acid addition salts.

Examples of suitable acids to form the nontoxic, pharmaceutically acceptable acid addition salts are mineral acids such as hydrochloric acid, hydrobromic acid, hydroiodic acid, nitric acid, sulfuric acid or phosphoric acid or organic acids such as acetic acid, formic acid, benzoic acid, maleic acid, fumaric acid, succinic acid, tartaric acid, citric acid, oxalic acid glyoxylic acid or aspartic acid or alkanesulfonic acids such as methanesulfonic acid or ethanesulfonic acid or arylsulfonic acids such as benzenesulfonic acid or p-toluenesulfonic acid or aryl carboxylic acids.

Examples of alkyl groups of 1 to 5 carbon atoms are methyl, ethyl, propyl, isopropyl, butyl, isobutyl, pentyl or tert.-butyl.

Among the preferred compounds of formula I are those wherein $R_1$ is methyl or hydrogen and $R_2$ is methyl and especially those wherein $R_1$ is hydrogen and $R_2$ is methyl. Specific preferred compounds of formula I are N,N-dimethyl-2-nitro-6,7-dihydro [5H] benzocycloheptene-7-methanamine, N-methyl-2-nitro-6,7-dihydro [5H] benzocycloheptene-7-methanamine, N-methyl-2-amino-6,7-dihydro [5H] benzocycloheptene-7-methanamine, N-methyl-2-methoxy-6,7-dihydro [5H] benzocycloheptene-7-methanamine and 7-methylaminomethyl-6,7-dihydro [5H] benzocycloheptane-2-ol and their non-toxic, pharmaceutically acceptable acid addition salts.

The compounds of formula I possess an asymetric carbon atom and therefor have two enantiomeric forms and may exist in the form of racemic mixtures or optically active isomers.

The novel process of the invention for the preparation of a compound of formula I wherein X is nitro comprises reacting 3-nitro-8,9-dihydro [5H] benzocycloheptene-5-one of the formula

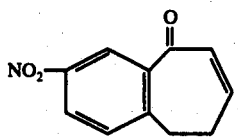

with acetone cyanhydrin of the formula

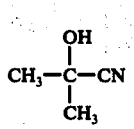

to obtain 3-nitro-5-oxo-6,7,8,9-tetrahydro [5H] benzocycloheptene-7-carbonitrile of the formula

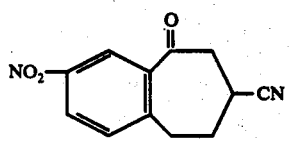

reducing the latter with diborane in an organic solvent to obtain 3-nitro-7-aminomethyl-6,7,8,9-tetrahydro [5H] benzocycloheptene-5-ol of the formula

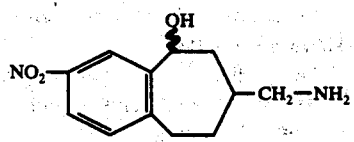

deshydrating the latter to form 2-nitro-6,7-dihydro [5H] benzocycloheptene-7-methanamine of the formula

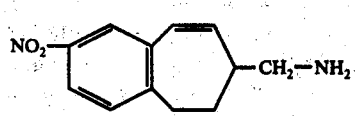

and either reacting the latter with formic aldehyde and sodium cyanoborohydride to obtain N,N-dimethyl-2-nitro-6,7-dihydro [5H] benzocycloheptene 7-methanamine of the formula

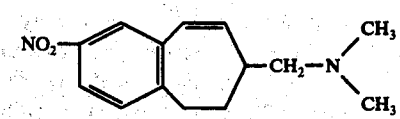

which may be reacted with an alkyl chloroformate of the formula

wherein Z is alkyl of 1 to 3 carbon atoms to obtain a compound of the formula

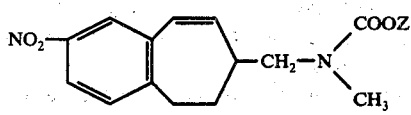 VIII and hydrolyzing the latter in an acid media to obtain N-methyl-2-nitro-6,7-dihydro [5H] benzocycloheptene-7-methanamine of the formula

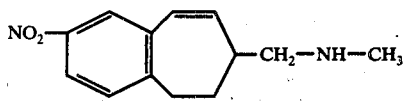 Ib or reacting the compound of formula VI in the presence of a base with an alkyl halide of the formula

R—X            IX wherein X is chlorine, bromine or iodine and R is alkyl of 1 to 5 carbon atoms to obtain a mixture of compounds of the formulae

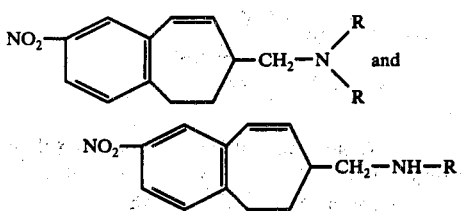

while separating the compounds by chromatography and optionally salifying the latter.

In a preferred embodiment of the said process, 3-nitro-8,9-dihydro [5H] benzocycloheptene-5-one is reacted with acetone cyanhydrin in an organic solvent such as methanol, the reduction of 3-nitro-5-oxo-6,7,8,9-tetrahydro [5H] benzocycloheptene-7-carbonitrile is effected in an organic solvent such as tetrahydrofuran, the deshydration of 3-nitro-7-aminomethyl-6,7,8,9-tetrahydro [5H] benzocycloheptene-5-ol is effected with polyphosporic acid, potassium bisulfate or a strong acid such as hydrochloric acid or sulfuric acid in an organic solvent such as dioxane, the reaction of 2-nitro-6,7-dihydro [5H] benzocycloheptene-7-methanamine is effected at room temperature in an organic solvent such as acetonitrile or tetrahydrofuran, the reaction of N,N-dimethyl-2-nitro-6,7-dihydro [5H] benzocycloheptene 7-methanamine with the alkyl chloroformate is effected in an organic solvent such as benzene, the acid hydrolysis of the product of formula VIII is effected with hydrobromic acid in a refluxing acetic acid medium and the reaction of 2-nitro-6,7-dihydro [5H] benzocycloheptene-7-methanamine with the alkyl halide is effected in the presence of a base such as potassium carbonate or triethylamine. The process of the invention for the preparation of a compound of formula I wherein X is amino, methoxy or hydroxy comprises reducing a compound of the formula

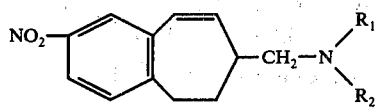 Ic wherein $R_1$ and $R_2$ have the above definition with a selective reducing agent to form a compound of the formula

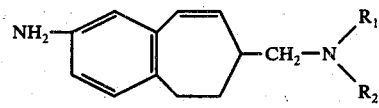 Id which may be recovered or reacted with nitrosyl sulfuric acid or sodium nitrite in a sulfuric acid solution to obtain a salt of the corresponding diazonium compound which is then treated with methanol to form a compound of the formula

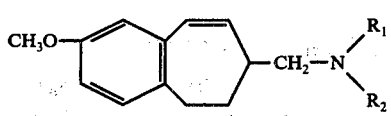 Ie or is decomposed to form a compound of the formula

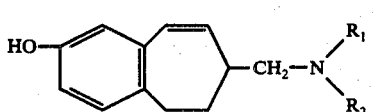 If

The products of formula Id, Ie, or If may be salified by known procedures.

In a preferred mode of the invention, the selective reducing agent is a mixture of stannous chloride and hydrochloric acid and the reaction with nitrosyl sulfuric acid is effected in an acetic acid medium and the diazonium salt is decomposed with sulfuric acid.

In a variation of the process of the invention, the compound of formula IV is reduced with sodium borohydride in an organic solvent to obtain a mixture of the cis and trans isomers of the formula

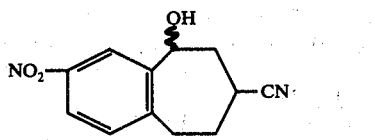 X which isomers can be optionally separated by chromatography and reacting the product with diborane in an organic solvent to form corresponding isomer or racemic mixture of the compound of formula V.

Preferably, the reduction of the compound of formula IV is effected in an organic solvent such as ethanol and the reduction of the compound of formula X is effected in an organic solvent such as tetrahydrofuran.

As indicated above, the racemic mixtures of the compounds of formula I may be separated by known methods such as chromatography and the basic compounds of formula I may be salified by reacting with a stoichiometric amount of the appropriate acid. The acid addition salts may be prepared without isolating the free base.

The novel antidepressant composition of the invention are comprised of at least one compound of formula I and their non-toxic, pharmaceutically acceptable acid addition salts and an inert pharmaceutical carrier or excipient. The compositions may be in the form of tablets, dragees, gelules, granules, suppositories or injectable solutions or suspensions prepared in the usual fashion.

Examples of suitable excipients are talc, arabic gum, lactose, starch, magnesium stearate, cacao butter, aqueous or non-aqueous vehicles, fatty bodies of animal or vegetable origin, paraffinic derivatives, glycols, diverse wetting agents or emulsifiers and preservatives.

Among the preferred compounds of formula I are those wherein $R_1$ is hydrogen or methyl and $R_2$ is methyl. Specific preferred compounds are N,N-dimethyl-2-nitro-6,7-dihydro [5H] benzocycloheptene-7-methanamine, N-methyl-2-nitro-6,7-dihydro [5H]benzocycloheptene-7-methanamine, N-methyl-2-amino-6,7-dihydro [5H] benzocycloheptene-7-methanamine, N-methyl-2-methoxy-6,7-dihydro [5H] benzocycloheptene-7-methanamine and 7-methylaminomethyl-6,7-dihydro [5H] benzocycloheptene-2-ol and their non-toxic, pharmaceutically acceptable acid addition salts.

The antidepressant compositions are useful for the treatment of depressions, melancholy, manic-depressive psychosis, reactional and exhaustive depressions, neurotic depressions as well as for the treatment of Parkinson's disease.

The novel method of the invention for inducing antidepressant activity in warm-blooded animals comprises administering to warm-blooded animals an antidepressantly effective amount of at least one compound of formula I and their non-toxic, pharmaceutically acceptable acid addition salts. The compounds may be administered orally, rectally or parenterally and the usual effective dose is 0.2 to 6 mg/kg depending upon the compound and the method of administration.

The novel intermediates of the invention are 3-nitro-5-oxo-6,7,8,9-tetrahydro [5H] benzocycloheptane-7-carbonitrile, 3-nitro-7-aminomethyl-6,7,8,9-tetrahydro [5H] benzocycloheptene-5-ol in the form of racemic mixtures or optical isomers and its acid addition salts, 2-nitro-6,7-dihydro [5H] benzocycloheptene-7-methanamine and compounds of the formulae VIII and X.

The product of formula II may be prepared by reacting the compound of the formula

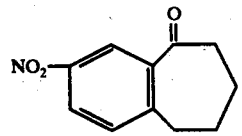

XI

[prepared as in J. Org., Vol. 26 (1961), p. 27] with cuprous bromide, bromine or a bromine complex in an organic solvent to obtain the compound of the formula

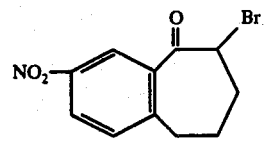

XII which is dehydrobrominated with a mixture of lithium bromide and lithium carbonate to obtain the compound of formula II. The bromine complex is preferably pyridinium perbromide.

In the following examples there are described several preferred embodiments to illustrate the invention. However, it should be understood that the invention is not intended to be limited to the specific embodiments.

EXAMPLE I

N,N,dimethyl-2-nitro-6,7-dihydro [5H] benzocycloheptene-7-methanamine

STEP A: 3-nitro-6-bromo-6,7,8,9-tetrahydro [5H] benzocycloheptene-5-one

A mixture of 935 g of cuprous bromide in 2.150 liters of ethyl acetate was heated to reflux and a solution of 430 g of 3-nitro-6,7,8,9-tetrahydro [5H] benzocycloheptene-5-one in 2.150 liters of chloroform was added thereto. 5 minutes after the addition was finished, the reaction began and the reflux became strong. After 1 hour, the mixture was cooled to 20° C. and was vacuum filtered and the filter was washed with chloroform. The filtrate was added to 3 liters of an aqueous saturated sodium bicarbonate solution and the mixture was decanted. The organic pulse was dried over sodium sulfate and was evaporated to dryness under reduced pressure. The residue was empasted 3 times with 450 ml of isopropyl ether and was dried in an oven at 35° C. to obtain 548 g of 3-nitro-6-bromo-6,7,8,9-tetrahydro [5H] benzocycloheptene-5-one in the form of cream crystals melting at 105° C.

STEP B: 3-nitro-8,9-dihydro [5H] benzocycloheptene-5-one

A mixture of 548 g of lithium carbonate and 548 of lithium bromide in 5.480 liters of dimethylformamide was heated to 100° C. and 548 g of 3-nitro-6-bromo-6,7,8,9-tetrahydro [5H] benzocycloheptene-5-one were added thereto over 5 minutes. The mixture was held at 100° C. for 45 minutes and was then poured into 25 liters of a mixture of water and ice. The mixture was vacuum filterd and the insolubles were extracted 8 times with 1 liter of methylene chloride. The organic phase was washed with water, dried over sodium sulfate and was evaporated to dryness under reduced pressure to obtain a red crystalline mass. The latter was empasted successively 3 times with 400 ml of ether, once with 400 ml of ethanol and once with 400 ml of ether and was dried at 40° C. to obtain 286.7 g of 3-nitro-8,9-dihydro [5H] benzocycloheptene-5-one in the form of orange-red crystals melting at 128° C.

STEP C: 3-nitro-5-oxo-6,7,8,9-tetrahydro [5H] benzocycloheptene-7-carbonitrile

A mixture of 50 g of 3-nitro-8,9-dihydro [5H] benzocycloheptene-5-one, 1200 ml of methanol, 120 ml of tetrahydrofuran, 100 ml of a 10% aqueous potassium carbonate and 50 ml of acetone cyanhydrin under nitrogen was refluxed for an hour in a bath at 90° C. and the mixture was concentrated to about 200 ml under reduced pressure. The mixture was cooled to 20° C. and was extracted with methylene chloride. The organic phase was washed with water, dried and distilled to dryness under reduced pressure. The 58 g of brown oil residue were crystallized from 50 ml of methanol and the mixture was vacuum filtered to obtain 46 g of 3-nitro-5-oxo-6,7,8,9-tetrahydro [5H] benzocycloheptene- 7-carbonitrile with a melting point of 107° C. and then 120° C.

Analysis: $C_{12}H_{10}N_2O_3$; molecular weight = 230.22 Calculated: %C 62.60, %H 4.38, %N 12.17. Found: %C 62.6, %H 4.4, %N 11.9.

STEP D: cis and trans isomers of 3-nitro-7-aminomethyl-6,7,8,9-tetrahydro [5H] benzocycloheptene-5-ol 20 g of 3-nitro-5-oxo-6,7,8,9-tetrahydro [5H] benzocycloheptene-7-carbonitrile were added under nitrogen to 200 ml of anhydrous tetrahydrofuran and diborane [prepared by introducing a solution of 23 g of sodium borohydride in 640 ml of diglyme at 20° C. over 4 hours into a solution of 118 g of a ether-boron trifluoride complex in 250 ml of diglyme (J.A.C.S., Vol. 82 (1960), p. 685] was bubbled into the mixture for 30 minutes at room temperature. The mixture was then heated for 3½ hours on a bath at 50° C. and was then cooled to 20° C. 100 ml of water were added thereto dropwise over 10 minutes followed by 50 ml of fuming hydrochloric acid. The mixture was refluxed for an hour and was cooled to 20° C. after which 100 ml of water were added. The mixture was extracted with ethyl acetate and the organic phase was washed with water. The combined aqueous phases were made alkaline at 10° C. with concentrated sodium hydroxide and was iced. The mixture was vacuum filtered and the white product was washed with water. The wash waters were washed with methylene chloride containing 20% of methanol and the organic phase was washed with water. The while precipitate from the aqueous phase was dissolved in 100 ml of water and the solution was added to the organic extracts. The mixture was dried over magnesium sulfate, filtered and evaporated to dryness under reduced pressure to obtain 14 g of a yellow oil which was crystallized from ethyl acetate to finally obtain 13 g of a mixture of cis and trans isomers of 3-nitro-7-aminomethyl-6,7,8,9-tetrahydro [5H] benzocycloheptene-5-ol melting at ≃150° C.

STEP E: 2-nitro-6,7-dihydro [5H] benzocycloheptene-7-methanamine hydrochloride A mixture of 10 g of the product of Step D in 100 ml of dioxane under nitrogen was heated to reflux and 20 ml of concentrated sulfuric acid were added thereto dropwise over 3 minutes. The mixture was stirred at reflux for 20 minutes and was then concentrated to 50 ml under reduced pressure. 300 ml of water were added and the neutral fraction was removed with ether. The aqueous phase was made alkaline at 10° C. with sodium hydroxide and was then extracted with methylene chloride. The organic extracts were dried and evaporated to dryness to obtain 10 g of 2-nitro-6,7-dihydro [5H] benzocycloheptene-7-methanamine in the form of a yellow oil.

The 10 g of said product were dissolved in 20 ml of ethyl acetate and a solution of ethyl acetate saturated with gaseous hydrochloric acid was added dropwise until the pH was acid to obtain 10 g of 2-nitro-6,7-dihydro [5H] benzocycloheptene-7-methanamine hydrochloride in the form of white crystals melting at 195° C. and then 210° C.

Analysis: $C_{12}H_{14}N_2O_2$. HCl; molecular weight = 254.72. Calculated: %C 56.58, %H 5.94, %N 11.00, %Cl 13.92. Found: %C 56.4, %H 6.0, %N 10.9, %Cl 13.6.

STEP F: N,N-dimethyl-2-nitro-6,7-dihydro [5H] benzocycloheptene-7-methanamine hydrochloride A mixture of 8.9 g of 2-nitro-6,7-dihydro [5H] benzocycloheptene-7-methanamine in 60 ml of acetonitrile and 19 ml of a 40% aqueous formic aldehyde solution under nitrogen was stirred at room temperature and then 6.3 g of sodium cyanoborohydride were added over 5 minutes. The mixture was stirred for 15 minutes at room temperature, was cooled and neutralized in 5 minutes with acetic acid. The mixture was stirred for 45 minutes at room temperature and was then evaporated to dryness. The residue was added to 75 ml of 2N sodium hydroxide solution and the mixture was extracted with methylene chloride. The organic extracts were washed with water, dried and evaporated to dryness under reduced pressure to obtain 9 g of a yellow oil which was taken up in 400 ml of ether. Activated carbon was added to the solution which was filtered and the filtrate was distilled to dryness under reduced pressure to obtain 8.9 g of N,N-dimethyl-2-nitro-6,7-dihydro [5H] benzocycloheptene-7-methanamine in the form of a colorless oil.

The said oil was dissolved in 10 ml of ethyl acetate and a solution of ethyl acetate saturated with gaseous hydrogen chloride was added at 10° C. until the pH was acid. The mixture was vacuum filtered to obtain 8.3 g of N,N-dimethyl-2-nitro-6,7-dihydro [5H] benzocycloheptene-7-methanamine hydrochloride in the form of white crystals melting at 215° C.

Analysis: $C_{14}H_{18}N_2O_2$. HCl; molecular weight = 282.77. Calculated: %C 59.46, %H 6.77, %N 9.91, %Cl 12.54. Found: %C 59.3, %H 7.0, %N 10.0, %Cl 12.6.

EXAMPLE 2

N,N-dimethyl-2-nitro-6,7-dihydro [5H] benzocycloheptene-7-methanamine hydrochloride

STEP A: cis and trans isomers of 3-nitro-5-hydroxy-6,7,8,9-tetrahydro-[5H] benzocycloheptene-7-carbonitrile.

10 g of sodium borohydride were added over 5 minutes under nitrogen to a mixture of 20 g of 3-nitro-5-oxo-6,7,8,9-tetrahydro [5H] benzocycloheptene-7-carbonitrile, 200 ml of ethanol and 20 ml of water and the mixture was stirred for one hour at room temperature and then evaporated to dryness under reduced pressure. 400 ml of water were added to the residue and the mixture was extracted with methylene chloride. The organic phase was washed with water, dried and evaporated to dryness under reduced pressure to obtain 18 g of raw product which were chromatographed over silica gel. Elution with a 9-1 ethyl acetate-triethylamine mixture yielded 2 fractions. The first fraction of 6.5 g of trans product occured in the form of a yellow oil with an Rf = 0.65 which was crystallized from ethyl acetate to obtain 4.5 g of trans 5-hydroxy-3-nitro-6,7,8,9-tetrahydro [5H] benzocycloheptene-7-carbonitrile in the form of white crystals melting at 160° C. The second fraction of 7.9 g of cis product occured in the form of a yellow oil with a Rf = 0.55 which crystallized from ethyl acetate to obtain 6.5 g of cis 5-hydroxy-3-nitro-6,7,8,9-tetrahydro [5H] benzocycloheptene-7-carbonitrile in the form of white crystals melting at 142° C.

STEP B: cis and trans isomers of 3-nitro-7-aminomethyl-6,7,8,9-tetrahydro [5H] benzocycloheptene-5-ol Diborane was bubbled through a mixture of 1 g of the cis isomer of Step A in 10 ml of anhydrous tetrahydrofuran under nitrogen for 30 minutes at room temperature and for 3½ hours in a bath at 50° C. and the mixture was cooled to 20° C. 10 ml of water were added thereto dropwise over 5 minutes followed by the addition of 5 ml of fuming hydrochloric acid and the mixture was refluxed for 1 hour and was then cooled. 30 ml of 0.5N hydrochloric acid were added thereto and the mixture was extracted with ethyl acetate. The organic extracts were washed with water and the combined aqueous phases were made alkaline with sodium hydroxide. The aqueous mixture was extracted with methylene chloride containing 25% of methanol and the organic extract was dried and evaporated to dryness under reduced pressure to obtain 820 mg of a colorless oil which was crystallized from methanol to obtain 600 mg of cis 3-nitro-7-aminomethyl-6,7,8,9-tetrahydro [5H] benzocycloheptene-5-ol in the form of white crystals melting at 208° C.

Analysis: $C_{12}H_{16}N_2O_3$; molecular weight = 236.26. Calculated: %C 61.00, %H 6.83, %N 11.86. Found: %C 61.3, %H 6.9, %N 11.6.

Using the same procedure but starting with 1 g of trans 3-nitro-5-hydroxy-6,7,8,9-tetrahydro [5H] benzocycloheptene-7-carbonitrile, there were obtained 700 mg of trans 3-nitro-7-aminomethyl-6,7,8,9-tetrahydro [5H] benzocycloheptene-5-ol in the form of white crystals melting at 156° C.

Analysis: $C_{12}H_{16}N_2O_3$; molecular weight = 236.26. Calculated: %C 61.00, %H 6.83, %N 11.86. Found: %C 60.8, %N 11.5.

STEP C: N,N-dimethyl-2-nitro-6,7-dihydro [5H] benzocycloheptene-7-methanamine hydrochloride Using the procedure of Steps E and F of Example 1, the cis and trans isomers of Step B were reacted to obtain N,N-dimethyl-2-nitro-6,7-dihydro [5H] benzocycloheptene-b 7-methanamine hydrochloride which was identical to the product of Step F of Example 1.

EXAMPLE 3

N-methyl-2-nitro-6,7-dihydro [5H] benzocycloheptene-7-methanamine hydrochloride

STEP A: ethyl methyl-[(2-nitro-6,7-dihydro [5H] benzocycloheptene -7-yl) methyl]-carbamate 50 ml of ethyl chloroformate were added dropwise over 5 minutes at 20° C. under nitrogen to a mixture of 7.9 g of N,N-dimethyl-2-nitro-6,7-dihydro [5H] benzocycloheptene-7-methanamine in 50 ml of benzene and the mixture was refluxed for 2 hours and then evaporated to dryness. The residue was extracted with ether and the ether phase was washed with N hydrochloric acid solution and then with water, was dried and distilled to dryness under reduced pressure to obtain 9 g of ethyl methyl-[(2-nitro-6,7-dihydro [5H] benzocycloheptene-7-yl) methyl]-carbamate in the form of a yellow oil.

STEP B: N-methyl-2-nitro-6,7-dihydro [5H] benzocycloheptene-7-methanamine hydrochloride 10 ml of 48% hydrobromic acid were added dropwise under nitrogen at 20° C. over 5 minutes to a mixture of 6.7 g of the product of Step A in 30 ml of acetic acid and the mixture was refluxed for 6 hours and was then cooled to 20° C. The mixture was poured into 500 ml of water and the neutral fraction was extracted with ether. The aqueous phase was made alkaline at 10° C. with sodium hydroxide and was extracted with ethyl acetate. The organic extracts were dried and evaporated to dryness to obtain 4 g of raw product which was dissolved in 200 ml of ether. The solution was treated with activated carbon and was filtered and the filtrate was evaporated to dryness to obtain 3.7 g of residue. The residue was chromatographed over silica gel and was eluted with a 7-3 chloroform-methanol mixture to obtain 2.8 g of N-methyl-2-nitro-6,7-dihydro [5H] benzocycloheptene-7-methanamine in the form of a colorless oil with an Rf = 0.4. The latter product was dissolved in 5 ml of ethyl acetate and a solution of ethyl acetate saturated with gaseous hydrochloric acid was added dropwise at 10° C. until the pH was acid. The mixture was vacuum filtered to obtain 2.9 g of N-methyl-2-nitro-6,7-dihydro [5H] benzocycloheptene-7-methanamine hydrochloride melting at 215° C.

Analysis: $C_{13}H_{17}N_2O_2Cl$; molecular weight = 268.75. Calculated: %C 58.09, %H 6.38, %N 10.43, %Cl 13.19. Found: %C 58.1, %H 6.6, %N 10.1, %Cl 13.2.

EXAMPLE 4 di-(N-methyl-2-amino-6,7-dihydro [5H] benzocycloheptene-7-methanamine) fumarate 6 g of the product of Example 3 were added under nitrogen to 40 ml of fuming hydrochloric acid and 18 g of stannous chloride were added thereto over 10 minutes while keeping the temperature at 20° C. The mixture was stirred at room temperature for 15 hours and was then poured into 100 ml of water. The mixture was made alkaline at 10° C. with sodium hydroxide and was extracted with methylene chloride. The organic extract was dried and evaporated to dryness under reduced pressure to obtain 3.8 g of N-methyl-2-amino-6,7-dihydro [5H] benzocycloheptene-7-methanamine in the form of a colorless oil.

The said product was dissolved in 20 ml of methanol and a solution of 1.08 g of fumaric acid in 20 ml of methanol was added thereto. The mixture was vacuum filtered to obtain 4.5 g of product which was crystallized from methanol to obtain 3 g of di-(N-methyl-2-amino-6,7-dihydro [5H] benzocycloheptene-7-methanamine) fumarate in the form of white crystals melting at 218° C.

Analysis: $C_{13}H_{18}N_2 \cdot C_2H_2O_2$ Calculated: %C 69.20, %H 7.74, %N 10.76. Found: %C 69.3, %H 7.6, %N 10.6.

EXAMPLE 5

N-methyl-2-methoxy-6,7-dihydro [5H] benzocycloheptene-7-methanamine hydrochloride 3.9 g of nitrosyl sulfuric acid were added over 10 minutes at 20° C. to a mixture of 5 g of the free base of Example 4 in 60 ml of acetic acid under nitrogen and the mixture was stirred for 2 hours at room temperature to obtain a solution of the salt of the corresponding diazonium compound. The said solution was added over 10 minutes at 20° C. to 300 ml of methanol and the mixture was refluxed for 45 minutes and then was evaporated to dryness. The residue was added to 200 ml of water and the neutral fraction was extracted with ether. The aqueous phase was made alkaline at 10° C. with sodium hydroxide and was then extracted with methylene chloride. The organic extract was washed with water, dried and evaporated to dryness to obtain 3.6 g of a dark oil. The latter was dissolved in 500 ml of ether and the solution was treated with activated carbon, filtered and evaporated to dryness to obtain 2.6 of N-methyl-2-methoxy-6,7-dihydro [5H] benzocycloheptene-7-methanamine in the form of a yellow oil.

The said base was dissolved in 30 ml of ethyl acetate cooled to 10° C. and then a solution of ethyl acetate saturated with gaseous hydrogen chloride was added dropwise to an acid pH. The mixture was vacuum filtered and the 2.5 g of raw product was crystallized from methyl ethyl ketone to obtain 2.2 of N-methyl-2-methoxy-6,7-dihydro [5H] benzocycloheptene-7-methanamine hydrochloride in the form of yellow crystals melting at 165°170° C.

Analysis: $C_{14}H_{19}NO \cdot HCl$; molecular weight = 253.77. Calculated: %C 66.26, %H 7.94, %N 5.52. Found: %C 66.3, %H 7.9, %N 5.7.

EXAMPLE 6

7-methylaminomethyl-6,7-dihydro [5H] benzocycloheptene-2-ol-hydrochloride

A solution of 1.6 g of sodium nitrite in 16 ml of water was added over 5 minutes at 5° C. to a mixture of 4.3 g of the free base of Example 4 in 43 ml of 6N sulfuric acid under nitrogen and the mixture was stirred at 5° C. for 30 minutes. The resulting solution was added over 3 minutes to a solution of 35 ml of water and 7 ml of concentrated sulfuric acid heated to 75° C. and the mixture was heated at 75° C. for 15 minutes and was then made alkaline at 10° C. with sodium hydroxide.

The non-phenolic phase was extracted with ether and the aqueous phase was acidified with concentrated hydrochloric acid. The aqueous phase was then made alkaline with concentrated ammonium hydroxide and the resulting precipitate was extracted with methylene chloride. The organic phase was dried and evaporated to dryness under reduced pressure to obtain 4.3 g of raw product which was chromatographed over slica gel. Elution with an 8-2 ethyl acetate-triethylamine mixture yielded 3.3 g of 7-methylaminomethyl-6,7-dihydro [5H] benzocycloheptene-2-ol.

The said base was dissolved in 10 ml of ethyl acetate and a solution of ethyl acetate saturated with gaseous hydrogen chloride was added dropwise thereto at 10° C. until the pH was 2 to obtain 3 g of 7-methylaminomethyl-6,7-dihydro [5H] benzocycloheptene-2-ol hydrochloride which melted at 208°–210° C. after crystallization from isopropanol.

Analysis: $C_{13}H_{17}NO \cdot HCl$; molecular weight = 239.74.

Calculated: %C 65.12, %H 7.57, %N 5.84, %Cl 14.79.

Found: %C 65.0, %H 7.9, %N 5.6, %Cl 14.5.

EXAMPLE 7

Tablets were prepared containing 25 mg of N,N-dimethyl-2-nitro-6,7-dihydro [5H] benzocycloheptene-7-methanamine hydrochloride and sufficient excipient of lactose, starch, talc and magnesium stearate for a final weight of 200 mg.

PHARMACOLOGICAL STUDY

A. Potentiation of effects of monoamine oxidase inhibitor

The administration of a monoamine oxidase inhibitor to mice induces a hyperactive movement of the animals which is able to be potentiated by an antidepressant. Using the procedure of Carlsson et al [Brain Research, Vol. 12 (1969), p. 456], a dose of 100 mg/kg of nialamide was intraperitoneally administered to mice 30 minutes before the intraperitoneal administration of the tested product and the values of actimetric measurements were recorded every 30 minutes for 6 hours. Potentiation of the effects of nial amide for the tested product was expressed in increasing number of + sign for a determined dose in mg/kg. The results are reported in Table I.

TABLE I

| Product of Example | Potentiation of Nialamide in mg/kg |
|---|---|
| 1 – 2 | +5 |
|  | +20 |
| 3 | +20 |
| 6 | +5 |
|  | +20 |

The results of Table I show that the tested products have an important potentiation of nialamide effect:

B. Potentiation of effects of L-dopa

The administration of L-dopa to mice pretreated 18 hours previously with iproniazide produced certain number of symptoms; muscular hypertonicity, hyperactivity, agitation crying, aggressiveness, salivation and exophthalmy. The intensity of these effects is potentiated by administration of an antidepressant one hour before the administration of L-dopa. Male mice received intraperitoneally 75 mg/kg of iproniazide 18 hours before the start of the test and the tested product was intraperitoneally administered in aqueous solution in increasing doses. One hour later, L-dopa was intraperitoneally administered at a dose of 100 mg/kg and the different symptoms were observed 15 and 30 minutes later. They were evaluated on a scale of 0 to 3 for each animal and the totals for each dose were determined. The $ED_{50}$ dose which potentiates by 50% the L-dopa effects was determined and is reported in Table II.

TABLE II

| Product of Example | $ED_{50}$ of mg/kg |
|---|---|
| 3 | 20 |
| 5 | 50 |
| 6 | 20 |

The results of Table II show that the tested products potentiate in an important manner the effects of L-dopa.

C. Acute Toxicity

The $DL_{50}$ dose which kills 50% of mice after intraperitoneal administration of the tested compound was determined 48 hours later and the $DL_{50}$ for the compounds is reported in Table III.

TABLE III

| Product of Example | $DL_{50}$ of mg/kg |
|---|---|
| 1 – 2 | 150 |
| 3 | 100 |
| 4 | 100 |
| 5 | 100 |
| 6 | 75 |

BIOCHEMICAL STUDY

A. Inhibition of Serotonine uptake in vitro

The inhibition of serotonine (5HT) uptake was measured in impure synaptosomes prepared from the entire brain of a female rat 19 to 21 days old using the technique of Kannengiesser et al [Biochemical Pharmacology, Vol. 22, (1973) p. 73]. Diverse concentrations of the products were placed in an incubator with the preparation at 37° C. for 5 minutes in the presence of 14 C-5HT at a concentration of $10^{-7}$ M. The 50% inhibiting concentration ($IC_{50}$), dose which inhibits by 50% the uptake of 14C-5HT in the synaptosomes was determined graphically and the $IC_{50}$ dose for the compounds is reported in Table IV.

TABLE IV

| Product of Example | Test in vitro I.C. 50 (M) |
| --- | --- |
| 1 - 2 | $6.3 \times 10^{-7}$ |
| 3 | $5.9 \times 10^{-7}$ |
| 4 | $6.8 \times 10^{-6}$ |
| 5 | $1.4 \times 10^{-6}$ |
| 6 | $9.8 \times 10^{-7}$ |

The results of Table IV show that the tested products have an interesting activity against serotonine.

Various modifications of the products and methods of the invention may be made without departing from the spirit or scope thereof and it should be understood that the invention is intended to be limited only as defined in the appended claims.

We claim:

1. A compound selected from the group consisting of 7-aminomethyl-benzocycloheptenes of the formula

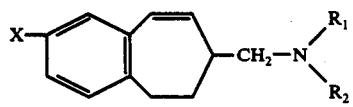

wherein X is selected from the group consisting of nitro, amino, methoxy and hydroxy, $R_1$ is selected from the group consisting of hydrogen and alkyl of 1 to 5 carbon atoms and $R_2$ is alkyl of 1 to 5 carbon atoms and their non-toxic, pharmaceutically acceptable acid addition salts.

2. A compound of claim 1 wherein $R_1$ is hydrogen or methyl and $R_2$ is methyl.

3. A compound of claim 2 wherein $R_1$ is hydrogen.

4. A compound selected from the group consisting of N,N-dimethyl-2-nitro-6,7-dihydro [5H] benzocycloheptene-7-methanamine and its non-toxic, pharmaceutically acceptable acid addition salts.

5. A compound selected from the group consisting of N-methyl-2-nitro-6,7-dihydro [5H] benzocycloheptene-7-methanamine and its non-toxic, pharmaceutically acceptable acid addition salts.

6. A compound selected from the group consisting of N-methyl-2-amino-6,7-dihydro [5H] benzocycloheptene-7-methanamine and its non-toxic, pharmaceutically acceptable acid addition salts.

7. A compound selected from the group consisting of N-methyl-2-methoxy-6,7-dihydro [5H] benzocycloheptene-7-methanamine and its non-toxic, pharmaceutically acceptable acid addition salts.

8. A compound of claim 1 selected from the group consisting of 7-methylaminomethyl-6,7-dihydro [5H] benzocycloheptene-2-ol and its non-toxic, pharmaceutically acceptable acid addition salts.

9. An antidepressant composition comprising an antidepressantly effective amount of at least one compound of claim 1 and an inert pharmaceutical carrier.

10. A composition of claim 9 wherein $R_1$ is hydrogen or methyl and $R_2$ is methyl.

11. A composition of claim 10 wherein $R_1$ is hydrogen.

12. A method of relieving depression in warm-blooded animals comprising administering to warm-blooded animals an antidepressantly effective amount of at least one compound of claim 1.

13. A method of claim 12 wherein $R_1$ is hydrogen or methyl and $R_2$ is methyl.

14. A method of claim 13 wherein $R_1$ is hydrogen.